United States Patent
Xu et al.

(10) Patent No.: US 9,534,285 B2
(45) Date of Patent: *Jan. 3, 2017

(54) PRECURSOR COMPOSITIONS FOR ATOMIC LAYER DEPOSITION AND CHEMICAL VAPOR DEPOSITION OF TITANATE, LANTHANATE, AND TANTALATE DIELECTRIC FILMS

(71) Applicant: Entegris, Inc., Billerica, MA (US)

(72) Inventors: Chongying Xu, New Milford, CT (US); Tianniu Chen, Westford, MA (US); Thomas M. Cameron, Newtown, CT (US); Jeffrey F. Roeder, Brookfield, CT (US); Thomas H. Baum, New Fairfield, CT (US)

(73) Assignee: ENTEGRIS, INC., Billerica, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/301,861

(22) Filed: Jun. 11, 2014

(65) Prior Publication Data

US 2014/0295071 A1 Oct. 2, 2014

Related U.S. Application Data

(63) Continuation of application No. 13/370,072, filed on Feb. 9, 2012, now Pat. No. 8,784,936, which is a
(Continued)

(51) Int. Cl.
*C23C 16/40* (2006.01)
*C23C 14/08* (2006.01)
(Continued)

(52) U.S. Cl.
CPC ............. *C23C 14/088* (2013.01); *C07F 17/00* (2013.01); *C23C 16/409* (2013.01); *C23C 16/45553* (2013.01)

(58) Field of Classification Search
None
See application file for complete search history.

(56) References Cited

U.S. PATENT DOCUMENTS 4,915,988 A 4/1990 Erbil
4,927,670 A 5/1990 Erbil
(Continued)

FOREIGN PATENT DOCUMENTS

EP 0904568 B1 4/2001
EP 1645656 A1 4/2006
(Continued)

OTHER PUBLICATIONS

Habermeier, H., "Thin films of perovskite-type complex oxides", "Materials Today", Oct. 2007, pp. 34-43, vol. 10, No. 10.
(Continued)

*Primary Examiner* — Joseph Miller, Jr.

(57) ABSTRACT

Barium, strontium, tantalum and lanthanum precursor compositions useful for atomic layer deposition (ALD) and chemical vapor deposition (CVD) of titanate thin films. The precursors have the formula $M(Cp)_2$, wherein M is strontium, barium, tantalum or lanthanum, and Cp is cyclopentadienyl, of the formula

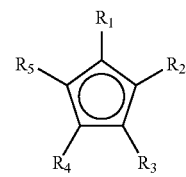

wherein each of $R_1$-$R_5$ is the same as or different from one another, with each being independently selected from among
(Continued)

hydrogen, $C_1$-$C_{12}$ alkyl, $C_1$-$C_{12}$ amino, $C_6$-$C_{10}$ aryl, $C_1$-$C_{12}$ alkoxy, $C_3$-$C_6$ alkylsilyl, $C_2$-$C_{12}$ alkenyl, $R^1R^2R^3NNR^3$, wherein $R^1$, $R^2$ and $R^3$ may be the same as or different from one another and each is independently selected from hydrogen and $C_1$-$C_6$ alkyl, and pendant ligands including functional group(s) providing further coordination to the metal center M. The precursors of the above formula are useful to achieve uniform coating of high dielectric constant materials in the manufacture of flash memory and other microelectronic devices.

13 Claims, 3 Drawing Sheets

Related U.S. Application Data continuation of application No. 12/619,165, filed on Nov. 16, 2009, now Pat. No. 8,206,784, which is a continuation of application No. 12/282,511, filed as application No. PCT/US2007/063825 on Mar. 12, 2007, now Pat. No. 7,638,074.

(60) Provisional application No. 60/781,291, filed on Mar. 10, 2006, provisional application No. 60/791,299, filed on Apr. 12, 2006, provisional application No. 60/844,867, filed on Sep. 15, 2006, provisional application No. 60/884,728, filed on Jan. 12, 2007.

(51) Int. Cl.
C07F 17/00 (2006.01)
C23C 16/455 (2006.01)

(56) References Cited

U.S. PATENT DOCUMENTS

| | | |
|---|---|---|
| 4,948,623 A | 8/1990 | Beach et al. |
| 4,960,916 A | 10/1990 | Pazik |
| 4,962,214 A | 10/1990 | Villacorta et al. |
| 5,204,057 A | 4/1993 | Ishigami et al. |
| 5,204,314 A | 4/1993 | Kirlin et al. |
| 5,225,561 A | 7/1993 | Kirlin et al. |
| 5,280,012 A | 1/1994 | Kirlin et al. |
| 5,453,494 A | 9/1995 | Kirlin et al. |
| 5,536,323 A | 7/1996 | Kirlin et al. |
| 5,555,154 A | 9/1996 | Uchikawa et al. |
| 5,711,816 A | 1/1998 | Kirlin et al. |
| 5,721,043 A | 2/1998 | Summerfelt et al. |
| 5,770,921 A | 6/1998 | Aoki et al. |
| 5,820,664 A | 10/1998 | Gardiner et al. |
| 5,837,417 A | 11/1998 | Rahman et al. |
| 5,840,897 A | 11/1998 | Kirlin et al. |
| 5,919,522 A | 7/1999 | Baum et al. |
| 6,002,036 A | 12/1999 | Kadokura |
| 6,024,847 A | 2/2000 | Rosenberg et al. |
| 6,025,222 A | 2/2000 | Kimura et al. |
| 6,087,500 A | 7/2000 | Fukuda et al. |
| 6,110,529 A | 8/2000 | Gardiner et al. |
| 6,110,531 A | 8/2000 | Paz de Araujo et al. |
| 6,111,122 A | 8/2000 | Paw et al. |
| 6,177,558 B1 | 1/2001 | Brennan et al. |
| 6,218,518 B1 | 4/2001 | Baum et al. |
| 6,277,436 B1 | 8/2001 | Stauf et al. |
| 6,287,965 B1 | 9/2001 | Kang et al. |
| 6,340,386 B1 | 1/2002 | Hendrix et al. |
| 6,342,445 B1 | 1/2002 | Marsh |
| 6,440,495 B1 | 8/2002 | Wade et al. |
| 6,479,100 B2 | 11/2002 | Jin et al. |
| 6,506,666 B2 | 1/2003 | Marsh |
| 6,511,706 B1 | 1/2003 | Hendrix et al. |
| 6,562,678 B1 | 5/2003 | Uchiyama et al. |
| 6,599,447 B2 | 7/2003 | Stauf et al. |
| 6,646,122 B1 | 11/2003 | Nuhlen et al. |
| 6,660,331 B2 | 12/2003 | Hendrix et al. |
| 6,673,646 B2 | 1/2004 | Droopad |
| 6,680,251 B2 | 1/2004 | Won et al. |
| 6,743,739 B2 | 6/2004 | Shimamoto et al. |
| 6,787,186 B1 | 9/2004 | Hintermaier |
| 6,849,122 B1 | 2/2005 | Fair |
| 6,984,591 B1 | 1/2006 | Buchanan et al. |
| 6,989,457 B2 | 1/2006 | Kamepalli et al. |
| 7,108,747 B1 | 9/2006 | Leskela et al. |
| 7,211,509 B1 | 5/2007 | Gopinath et al. |
| 7,250,367 B2 | 7/2007 | Vaartstra et al. |
| 7,285,308 B2 | 10/2007 | Hendrix et al. |
| 7,300,038 B2 | 11/2007 | Gregg et al. |
| 7,635,441 B2 | 12/2009 | Kadokura et al. |
| 7,638,074 B2 | 12/2009 | Xu et al. |
| 7,790,629 B2 | 9/2010 | Holme et al. |
| 8,034,407 B2 | 10/2011 | Hendrix et al. |
| 8,092,721 B2 | 1/2012 | Gatineau et al. |
| 8,206,784 B2 | 6/2012 | Xu et al. |
| 8,455,049 B2 | 6/2013 | Cameron et al. |
| 2002/0004266 A1 | 1/2002 | Hashimoto et al. |
| 2002/0067917 A1 | 6/2002 | Takamatsu et al. |
| 2002/0090815 A1 | 7/2002 | Koike et al. |
| 2002/0146513 A1 | 10/2002 | Jin et al. |
| 2003/0012876 A1 | 1/2003 | Min et al. |
| 2003/0020122 A1 | 1/2003 | Joo et al. |
| 2003/0032238 A1 | 2/2003 | Kim et al. |
| 2003/0038594 A1 | 2/2003 | Seo et al. |
| 2003/0072882 A1 | 4/2003 | Niinisto et al. |
| 2003/0129306 A1 | 7/2003 | Wade et al. |
| 2003/0165615 A1 | 9/2003 | Aaltonen et al. |
| 2003/0205823 A1 | 11/2003 | Leu et al. |
| 2004/0038808 A1 | 2/2004 | Hampden-Smith et al. |
| 2004/0043149 A1 | 3/2004 | Gordon et al. |
| 2004/0166671 A1 | 8/2004 | Lee et al. |
| 2004/0197946 A1 | 10/2004 | Vaartstra et al. |
| 2004/0211998 A1 | 10/2004 | Araujo et al. |
| 2004/0214354 A1 | 10/2004 | Marsh et al. |
| 2004/0238861 A1 | 12/2004 | Hwang et al. |
| 2005/0009325 A1 | 1/2005 | Chung et al. |
| 2005/0153073 A1 | 7/2005 | Zheng et al. |
| 2005/0186341 A1 | 8/2005 | Hendrix et al. |
| 2005/0208699 A1 | 9/2005 | Furkay et al. |
| 2005/0217575 A1 | 10/2005 | Gealy et al. |
| 2005/0277780 A1 | 12/2005 | Gordon et al. |
| 2006/0006449 A1 | 1/2006 | Jeong et al. |
| 2006/0027451 A1 | 2/2006 | Park et al. |
| 2006/0035462 A1 | 2/2006 | Millward |
| 2006/0049447 A1 | 3/2006 | Lee et al. |
| 2006/0115595 A1 | 6/2006 | Shenai-Khatkhate et al. |
| 2006/0118968 A1 | 6/2006 | Johnston et al. |
| 2006/0128150 A1 | 6/2006 | Gandikota et al. |
| 2006/0138393 A1 | 6/2006 | Seo et al. |
| 2006/0172067 A1 | 8/2006 | Ovshinsky et al. |
| 2006/0172083 A1 | 8/2006 | Lee et al. |
| 2006/0180811 A1 | 8/2006 | Lee et al. |
| 2006/0275545 A1 | 12/2006 | Yoshinaka et al. |
| 2006/0288928 A1 | 12/2006 | Eom et al. |
| 2007/0004226 A1 | 1/2007 | Tweet et al. |
| 2007/0049021 A1 | 3/2007 | Basceri |
| 2007/0053139 A1 | 3/2007 | Zhang et al. |
| 2007/0054487 A1 | 3/2007 | Ma et al. |
| 2007/0116888 A1 | 5/2007 | Faguet |
| 2007/0154637 A1 | 7/2007 | Shenai-Khatkhate et al. |
| 2007/0190362 A1 | 8/2007 | Weidman |
| 2008/0194088 A1 | 8/2008 | Srinivasan et al. |
| 2008/0242111 A1 | 10/2008 | Holme et al. |
| 2008/0254218 A1 | 10/2008 | Lei et al. |
| 2008/0254232 A1 | 10/2008 | Gordon et al. |
| 2008/0317972 A1 | 12/2008 | Hendriks et al. |
| 2009/0001618 A1 | 1/2009 | Kadokura et al. |
| 2009/0002917 A1 | 1/2009 | Kil et al. |
| 2009/0004383 A1 | 1/2009 | Kadokura et al. |
| 2009/0058953 A1 | 3/2009 | Arakawa et al. |
| 2009/0074965 A1 | 3/2009 | Xu et al. |
| 2009/0087561 A1 | 4/2009 | Chen et al. |
| 2009/0215225 A1 | 8/2009 | Stender et al. |
| 2009/0275164 A1 | 11/2009 | Chen et al. |

(56) References Cited

U.S. PATENT DOCUMENTS

| | | | |
|---|---|---|---|
| 2009/0321733 | A1 | 12/2009 | Gatineau et al. |
| 2010/0015800 | A1 | 1/2010 | Hara et al. |
| 2010/0062150 | A1 | 3/2010 | Xu et al. |
| 2010/0095865 | A1 | 4/2010 | Xu et al. |
| 2010/0291299 | A1 | 11/2010 | Cameron et al. |
| 2011/0195188 | A1 | 8/2011 | Hendrix et al. |
| 2011/0215679 | A1 | 9/2011 | Naono |
| 2011/0292134 | A1 | 12/2011 | Sasaki et al. |
| 2012/0064719 | A1 | 3/2012 | Lubguban, Jr. et al. |
| 2012/0141675 | A1 | 6/2012 | Xu et al. |
| 2013/0251918 | A1 | 9/2013 | Cameron et al. |

FOREIGN PATENT DOCUMENTS

| | | | |
|---|---|---|---|
| EP | 1798307 | A1 | 6/2007 |
| EP | 2000561 | A1 | 12/2008 |
| JP | 2-225317 | A | 9/1990 |
| JP | 7-70747 | A | 3/1995 |
| JP | 7-249616 | A | 9/1995 |
| JP | 10-125237 | A | 5/1998 |
| JP | 10-273779 | A | 10/1998 |
| JP | 2004-527651 | A | 9/2004 |
| JP | 2006-37123 | A | 2/2006 |
| KR | 10-0443350 | B1 | 7/2004 |
| KR | 10-2008-0079514 | A | 9/2008 |
| SU | 768457 | A | 10/1980 |
| WO | 0015865 | A1 | 3/2000 |
| WO | 0166834 | A2 | 9/2001 |
| WO | 2004046417 | A2 | 6/2004 |
| WO | 2006012052 | A2 | 2/2006 |
| WO | 2007064376 | A2 | 6/2007 |
| WO | 2008088563 | A2 | 7/2008 |
| WO | 2008117582 | A1 | 10/2008 |
| WO | 2009020888 | A1 | 2/2009 |

OTHER PUBLICATIONS

Ju, Y., et al., "Growth of Thin-Film Layered Perovskite Cathodes by Pulsed Laser Deposition and their Electrochemical Studies in IT-SOFCs", "Journal of the Electrochemical Society", Apr. 18, 2014, pp. F698-F702, vol. 161, No. 6.

Marozau, I., et al., "RF-plasma assisted pulsed laser deposition of nitrogen-doped SrTiO3 thin films", "Appl Phys A", Jun. 13, 2008, pp. 721-727, vol. 93.

Anderson, Q., et al., "Synthesis and Characterization of the First Pentaphenylcyclopentadienyl Copper(I) Complex, (Ph5Cp)Cu(PPh3)", "Organometallics", 1998, pp. 4917-4920, vol. 17.

Artaud-Gillet, M., et al., "Evaluation of copper organometallic sources for CuGaSe2 photovoltaic applications", "Journal of Crystal Growth", 2003, pp. 163-168, vol. 248.

Burns, C., et al., "Organometallic Coordination Complexes of the BIS (Pentamethylcyclopentadienyl)-Alkaline Earth Compounds, (ME5C5)2MLN, Where M is Mg, Ca, Sr, or Ba and ME5C5BECL", "Journal of Organometallic Chemistry", 1987, pp. 31-37, vol. 325.

Christen, H., et al., "Semiconducting epitaxial films of metastable SrRu0.5Sn0.5O3 grown by pulsed laser deposition", "Applied Physics Letters", 1997, pp. 2147-2149 (Title and Abstract), vol. 70, No. 16.

Hatanpaa, T., et al., "Synthesis and characterisation of cyclopentadienyl complexes of barium: precursors for atomic layer deposition of BaTiO3", "Dalton Trans.", Mar. 22, 2004, pp. 1181-1188, vol. 8.

Holme, T., et al., "Atomic Layer Deposition and Chemical Vapor Deposition Precursor Selection Method Application to Strontium and Barium Precursors", "J. Phys. Chem.", Jul. 27, 2007, pp. 8147-8151, vol. 111, No. 33.

Kirlin, P., et al., "Thin Films of Barium Fluoride Scintillator Deposited by Chemical Vapor Deposition", "Nuclear Instruments and Methods in Physics Research", 1990, pp. 261-264, vol. A289.

Kirlin, P., et al., "Growth of High Tc YBaCuO Thin Films by Metalorganic Chemical Vapor Deposition", "SPIE", 1989, pp. 115-127, vol. 1187.

Kosola, A., et al., "Effect of annealing in processing of strontium titanate thin films by ALD", "Applied Surface Science", 2003, pp. 102-112, vol. 211.

Kvyatkovskii, O., "On the Nature of Ferroelectricity in Sr1-xAxTiO3 and KTa1-xNbxO3 Solid Solutions", "Physics of the Solid State", 2002, pp. 1135-1144, vol. 44, No. 6.

Leskela, M., et al., "Atomic layer deposition chemistry: recent developments and future challenges", "Angew. Chem. Int. Ed.", Nov. 24, 2003, pp. 5548-5554, vol. 42, No. 45.

Lu, H., et al., "Evolution of itinerant ferromagnetism in SrxPb1-xRuO3 (0 less than or equal to x less than or equal to 1): Interplay between Jahn-Teller distortion and A-site disorder", "Applied Physics Letters", Mar. 22, 2011, pp. 1-3, vol. 98, No. 122503.

Macomber, D., et al., "(n5-Cyclopentadienyl)- and (n5-Pentamethylcyclopentadienyl)copper Compounds Containing Phosphine, Carbonyl, and n2-Acetylenic Ligands", "J. Am. Chem. Soc.", 1983, pp. 5325-5329, vol. 105.

McCormick, M., et al., "Solution Synthesis of Calcium, Strontium, and Barium Metallocenes", "Polyhedran", 1988, pp. 725-730, vol. 7, No. 9.

Niinistoe, J., et al., "Atomic Layer Deposition of High-k Oxides of the Group 4 Metals for Memory Applications", "Advanced Engineering Materials", Mar. 9, 2009, pp. 223-234, vol. 11, No. 4.

Papadatos, F., et al., "Characterization of Ruthenium and Ruthenium Oxide Thin Films deposited by Chemical Vapor Deposition for CMOS Gate Electrode Applications", "Mat. Res. Soc. Symp. Proc.", 2003, pp. N3.3.1-N3.3.6, vol. 745.

Ren, H., et al., "Synthesis and structures of cyclopentadienyl N-heterocyclic carbene copper(I) complexes", "Journal of Organometallic Chemistry", Jun. 21, 2006, pp. 4109-4113, vol. 691.

Selg, P., et al., "Solution Infrared Spectroscopic Studies on Equilibrium Reactions of Co With the Decamethylmetallocenes CP2MII, Where M=Mg, Ca, Sr, Ba, Sm, Eu, Yb", "Organometallics", Jun. 22, 2002, pp. 3100-3107, vol. 21, No. 15.

Singh, R., et al., "In-Situ Processing of Epitaxial Y—Ba—Cu—O High Tc Superconducting Films on (100) SrTiO3 and (100) Ys—ZrO2 Substrates at 500-650 Degrees Celsius", "Applied Physics Letters", May 29, 1989, pp. 2271-2273, vol. 54, No. 22.

Vehkamaki, M., et al., "Growth of SrTiO3 and BaTiO3 Thin Films by Atomic Layer Deposition", "Electrochemical Solid-State Letters", Aug. 5, 1999, pp. 504-506, vol. 2, No. 10.

Vehkamaki, M., et al., "Atomic Layer Deposition of SrTiO3 Thin Films from a Novel Strontium Precursor-Strontium-bis(triisopropylcyclopentadienyl)", "Chemical Vapor Deposition", Mar. 2001, pp. 75-80, vol. 7, No. 2.

Wu, L., et al., "Humidity Sensitivity of Sr(Sn, Ti)03 Ceramics", "Journal of Electronic Materials", 1990, pp. 197-200, vol. 19, No. 2.

Hanusa, T., "Ligand Influences on Structure and Reactivity in Organoalkaline-Earth Chemistry", Chem. Rev., May 1993, pp. 1023-1036, vol. 93.

PRECURSOR COMPOSITIONS FOR ATOMIC LAYER DEPOSITION AND CHEMICAL VAPOR DEPOSITION OF TITANATE, LANTHANATE, AND TANTALATE DIELECTRIC FILMS

CROSS-REFERENCE TO RELATED APPLICATIONS

This is a continuation of U.S. patent application Ser. No. 13/370,072, filed Feb. 9, 2012, which is a continuation of U.S. patent application Ser. No. 12/619,165, filed Nov. 16, 2009, now U.S. Pat. No. 8,206,784, which is continuation of U.S. patent application Ser. No. 12/282,511, now U.S. Pat. No. 7,638,074, filed on Sep. 10, 2008, which is a United States national phase, filed under the provisions of 35 USC §371, of International Application No. PCT/US07/63825 filed Mar. 12, 2007, which in turn claims the benefit and priority of U.S. Provisional Patent Application No. 60/781,291 filed Mar. 10, 2006; U.S. Provisional Patent Application No. 60/791,299 filed Apr. 12, 2006; U.S. Provisional Patent Application No. 60/844,867 filed Sep. 15, 2006; and U.S. Provisional Patent Application No. 60/884,728 filed Jan. 12, 2007. The disclosures of such U.S. applications, national phase application, international application and U.S. provisional applications are hereby incorporated herein by reference in their respective entireties, for all purposes.

BACKGROUND OF THE INVENTION

Field of the Invention

The present invention relates to precursor compositions having utility for atomic layer deposition and chemical vapor deposition of titanate, lanthanate, and tantalate thin films, e.g., in the manufacture of microelectronic devices, as well as to processes of making and using such precursors, to products formed using such precursor compositions, and to precursor supply systems comprising such precursor compositions in packaged form.

Description of the Related Art

Strontium titanate ($SrTiO_3$), barium titanate ($BaTiO_3$) and barium strontium titanates ($Ba_xSr_{1-x}TiO_3$ where $0 \leq x \leq 1$) are high dielectric constant materials that are potentially useful in future generation flash memories as well as other microelectronic products. Lanthanum oxides ($La_2O_3$), lanthanum tantalates ($La_xTa_yO_z$ where x, y, and z denote oxides of varying composition), and lanthanum titanates (e.g. $LaTiO_3$) represent another class of high dielectric constant materials potentially useful on future generation microelectronic devices. Uniform coating involving greater than 90% step coverage on high aspect ratio structures is required for such titanate materials to achieve requisite high capacity in flash memory device applications.

Atomic layer deposition (ALD) is currently being explored as a technique for achieving such step coverage, using strontium β-diketonates and titanium β-diketonates as precursors. It is difficult, however, to achieve satisfactory uniform coating of strontium titanate thin films using the β-diketonate precursors that have been developed to date. Similar deficiencies are encountered when chemical vapor deposition (CVD) is used as a deposition technique to form such titanate films.

The art continues to seek new precursors for deposition of thin film titanates, lanthanates and tantalates such as strontium titanate, barium titanate, barium strontium titanate, lanthanum oxide, lanthanum tantalate, and lanthanum titanate.

SUMMARY OF THE INVENTION

The present invention relates to barium, strontium, tantalum and lanthanum precursors having utility for atomic layer deposition of titanate films useful in the manufacture of microelectronic devices such as flash memories. The invention further relates to methods of making and using such precursors, to supply systems for selective dispensing of such precursors, and to microelectronic device products fabricated with the use of such precursors.

In one aspect, the present invention relates to precursors having the formula $M(Cp)_2$, wherein M is strontium or barium, precursors having the formula $X_3M(Cp)_2$ wherein M is tantalum and X is H or $Si(R_a)_3$, wherein each $R_a$ can be the same as or different from the other(s), and each is independently selected from among $C_1$-$C_6$ alkyl and $C_6$-$C_{10}$ aryl; and precursors having the formula $M(Cp)_3$ wherein M is lanthanum, and wherein Cp is cyclopentadienyl, of the formula

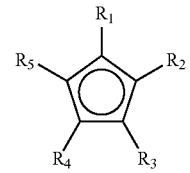

wherein each of $R_1$-$R_5$ is the same as or different from one another, with each being independently selected from among hydrogen, $C_1$-$C_{12}$ alkyl, $C_1$-$C_{12}$ amino, $C_6$-$C_{10}$ aryl, $C_1$-$C_{12}$ alkoxy, $C_3$-$C_6$ alkylsilyl, $C_2$-$C_{12}$ alkenyl (such term being intended to be broadly construed to include substituents containing linear, branched, and/or cyclic moieties containing ethylenic unsaturation, e.g., vinyl, allyl, cyclic-ene species, etc., and substituents containing various types of such moieties therein, e.g., tetramethylpentadienylvinyl), $R^1R^2R^3NNR^3$, wherein $R^1$, $R^2$ and $R^3$ may be the same as or different from one another and each is independently selected from hydrogen and $C_1$-$C_6$ alkyl, and pendant ligands including functional group(s) providing further coordination to the metal center, such as, for example, alkoxyalkyl, aryloxyalkyl, imidoalkyl, and acetylalkyl, wherein suitable groups in these classes include those of the following formulae:

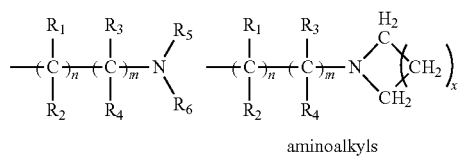

aminoalkyls wherein: the methylene (—$CH_2$—) moiety could alternatively be another divalent hydrocarbyl moiety; each of $R_1$-$R_4$ is the same as or different from one another, with each being independently selected from among hydrogen and $C_1$-$C_6$ alkyl and $C_6$-$C_{10}$ aryl; each of $R_5$ and $R_6$ is the same as or different from the other, with each being independently selected from among $C_1$-$C_6$ alkyl; n and m are each selected independently from 0 to 4 with the proviso that m and n cannot be 0 at the same time, and x is selected from 1 to 5;

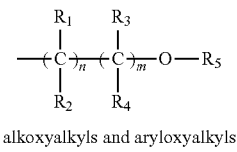

alkoxyalkyls and aryloxyalkyls wherein each of $R_1$-$R_4$ is the same as or different from one another, with each being independently selected from among hydrogen, $C_1$-$C_6$ alkyl, and $C_6$-$C_{10}$ aryl; $R_5$ is selected from among $C_1$-$C_6$ alkyl, and $C_6$-$C_{10}$ aryl; and n and m are selected independently from 0 to 4, with the proviso that m and n cannot be 0 at the same time;

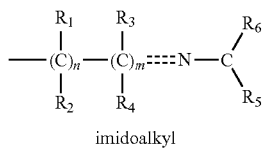

imidoalkyl wherein each of $R_1$-$R_6$ is the same as or different from one another, with each being independently selected from among hydrogen, $C_1$-$C_6$ alkyl, and $C_6$-$C_{10}$ aryl; and n and m are selected independently from 0 to 4, with the proviso that m and n cannot be 0 at the same time;

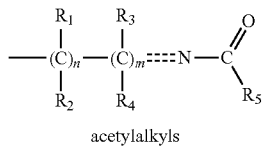

acetylalkyls wherein each of $R_1$-$R_4$ is the same as or different from one another, with each being independently selected from among hydrogen, $C_1$-$C_6$ alkyl, and $C_6$-$C_{10}$ aryl; $R_5$ is selected from among $C_1$-$C_6$ alkyl, and $C_6$-$C_{10}$ aryl; and n and m are selected independently from 0 to 4, with the proviso that m and n cannot be 0 at the same time.

As used herein, the identification of a carbon number range, e.g., in $C_1$-$C_6$ alkyl or $C_6$-$C_{10}$ aryl, is intended to include each of the component carbon number moieties within such range. Accordingly, $C_1$-$C_6$ alkyl is intended to include methyl, ethyl, propyl, butyl, pentyl and hexyl, including a straight chain as well as branched groups of such types. It therefore is to be appreciated that identification of a carbon number range, e.g., $C_1$-$C_6$, as broadly applicable to a substituent moiety, enables, in specific embodiments of the invention, the carbon number range to be further restricted, as a sub-group of moieties having a carbon number range within the broader specification of the substituent moiety. By way of example, the carbon number range e.g., $C_1$-$C_6$ alkyl, may be more restrictively specified, in particular embodiments of the invention, to encompass sub-ranges such as $C_1$-$C_4$ alkyl, $C_2$-$C_6$ alkyl, $C_2$-$C_4$ alkyl, $C_3$-$C_5$ alkyl, or any other sub-range within the broad carbon number range.

In another aspect, the invention relates to precursor composition, comprising such precursor in a solvent medium.

A further aspect of the invention relates to a method of forming a barium-, lanthanum- and/or strontium-containing material on a substrate, comprising contacting the substrate with a vapor of a precursor as described above, to deposit barium, lanthanum and/or strontium on the substrate from said vapor.

A still further aspect of the invention relates to an atomic layer deposition process for forming a barium, lanthanum and/or strontium titanate on a substrate, comprising:
(a) contacting the substrate with a titanium source under conditions producing a coating of titanium on the substrate;
(b) contacting the titanium-coated substrate with an oxidant or water to form a hydroxylated surface;
(c) contacting the hydroxylated surface with a barium, lanthanum and/or strontium precursor of the present invention, under conditions producing a coating of barium and/or strontium thereon;
(d) contacting the barium, lanthanum and/or strontium-coated substrate with an oxidant or water to form a hydroxylated surface; and
(e) repeating steps (a) through (d) for sufficient number of repetitions to produce a barium, lanthanum and/or strontium titanate film of predetermined thickness.

In another aspect, the invention relates to a barium, lanthanum and/or strontium supply package, comprising a vessel enclosing an interior volume holding a barium, lanthanum and/or strontium precursor as described above.

A further aspect of the invention relates to an atomic layer deposition process, comprising pulsing of a vapor of a titanium precursor into a deposition reactor, purging the reactor to remove excess titanium precursor, pulsing water vapor into the reactor, optionally with an oxidant, pulsing a barium, lanthanum and/or strontium source into the reactor, purging the reactor to remove excess barium, lanthanum and/or strontium precursor, and pulsing water vapor into the reactor, optionally with an oxidant.

Additional aspects of the invention relate to forming strontium-, lanthanum- and/or barium-containing films on substrates using the precursors described above, involving the use of chemical vapor deposition or atomic layer deposition, e.g., contacting of a microelectronic device substrate with a vapor of a precursor of the invention.

Other aspects, features and embodiments of the invention will be more fully apparent from the ensuing disclosure and appended claims.

DETAILED DESCRIPTION OF THE INVENTION, AND PREFERRED EMBODIMENTS THEREOF

Figure 1:
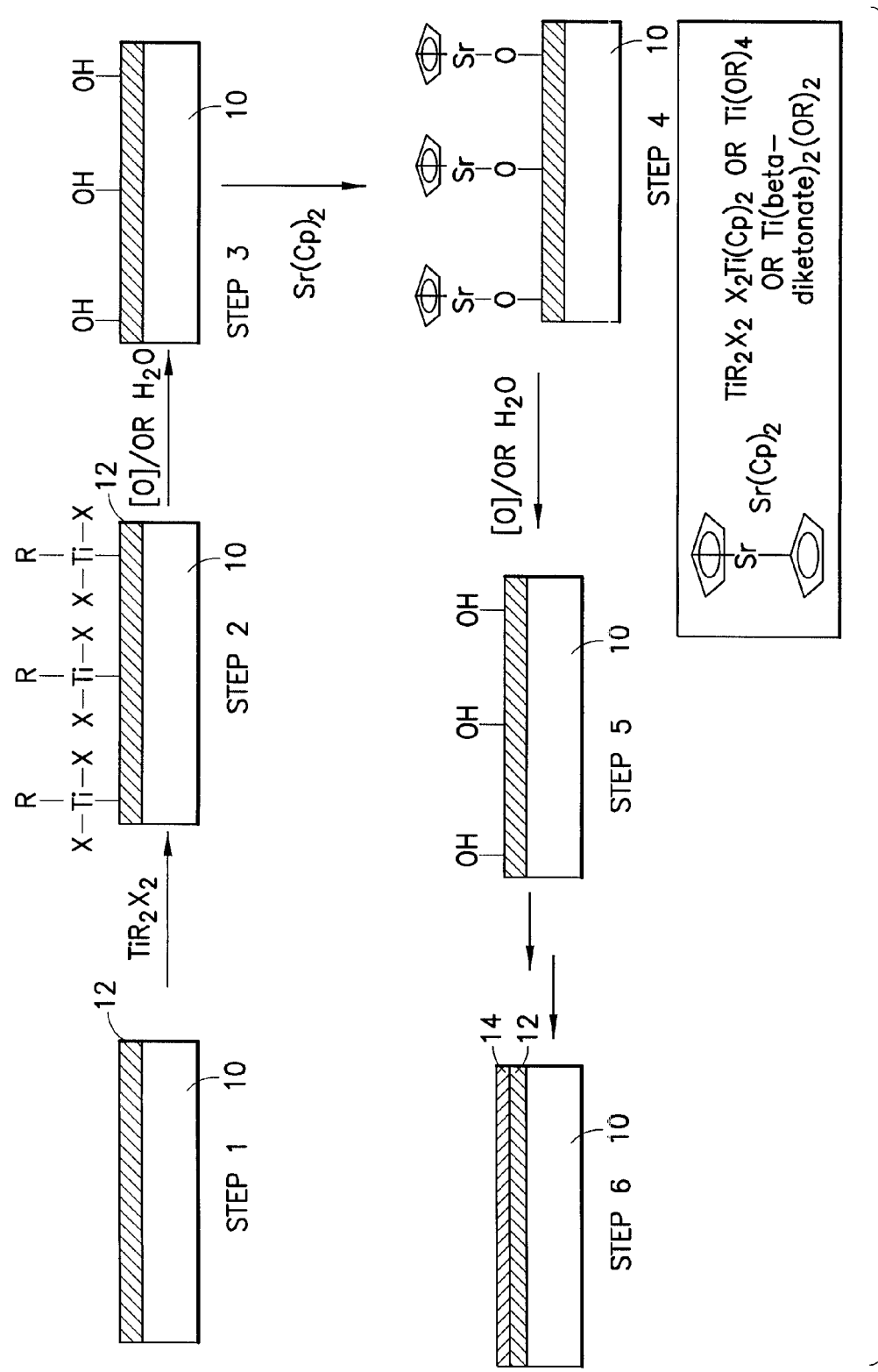
FIG. 1 is a schematic representation of an atomic layer deposition process utilizing a precursor of the present invention.

The present invention relates to barium, strontium, tantalum and lanthanum precursors having utility for atomic layer deposition of titanate films useful in the manufacture of microelectronic devices such as flash memories. The invention further relates to methods of making and using such precursors, to supply systems for selective dispensing of such precursors, and to microelectronic device products fabricated with the use of such precursors.

In a specific aspect, the present invention relates to precursors having the formula $M(Cp)_2$, wherein M is strontium or barium, precursors having the formula $X_3M(Cp)_2$ wherein M is tantalum and X is H or $Si(R_a)_3$, wherein each $R_a$ can be the same as or different from the other(s), and each is independently selected from among $C_1$-$C_6$ alkyl and $C_6$-$C_{10}$ aryl; and precursors having the formula $M(Cp)_3$ wherein M is lanthanum, and wherein Cp is cyclopentadienyl of the formula

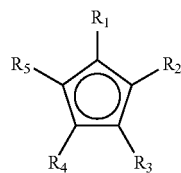

wherein each of $R_1$-$R_5$ is the same as or different from one another, with each being independently selected from among hydrogen, $C_1$-$C_{12}$ alkyl, $C_1$-$C_{12}$ amino, $C_6$-$C_{10}$ aryl, $C_1$-$C_{12}$ alkoxy, $C_3$-$C_6$ alkylsilyl, $C_2$-$C_{12}$ alkenyl, $R^1R^2R^3NNR^3$, wherein $R^1$, $R^2$ and $R^3$ may be the same as or different from one another and each is independently selected from hydrogen and $C_1$-$C_6$ alkyl, and pendant ligands including functional group(s) providing further coordination to the metal center, such as, for example, aminoalkyl, alkoxyalkyl, aryloxyalkyl, imidoalkyl, and acetylalkyl, wherein suitable groups in these classes may for example include those of the following formulae:

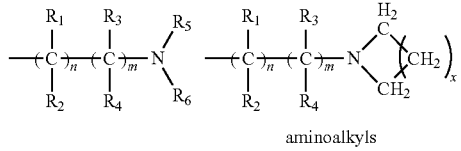

aminoalkyls wherein each of $R_1$-$R_4$ is the same as or different from one another, with each being independently selected from among hydrogen and $C_1$-$C_6$ alkyl and $C_6$-$C_{10}$ aryl; each of $R_5$ and $R_6$ is the same as or different from the other, with each being independently selected from among $C_1$-$C_6$ alkyl; n and m are each selected independently from 0 to 4 with the proviso that m and n cannot be 0 at the same time, and x is selected from 1 to 5;

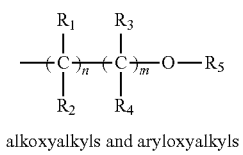

alkoxyalkyls and aryloxyalkyls wherein each of $R_1$-$R_4$ is the same as or different from one another, with each being independently selected from among hydrogen, $C_1$-$C_6$ alkyl, and $C_6$-$C_{10}$ aryl; $R_5$ is selected from among $C_1$-$C_6$ alkyl, and $C_6$-$C_{10}$ aryl; and n and m are selected independently from 0 to 4, with the proviso that m and n cannot be 0 at the same time;

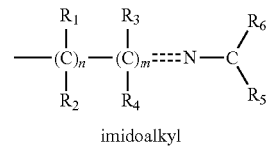

imidoalkyl wherein each of $R_1$-$R_6$ is the same as or different from one another, with each being independently selected from among hydrogen, $C_1$-$C_6$ alkyl, and $C_6$-$C_{10}$ aryl; and n and m are selected independently from 0 to 4, with the proviso that m and n cannot be 0 at the same time;

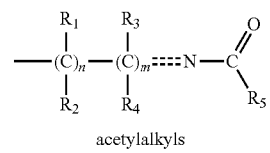

acetylalkyls wherein each of $R_1$-$R_4$ is the same as or different from one another, with each being independently selected from among hydrogen, $C_1$-$C_6$ alkyl, and $C_6$-$C_{10}$ aryl; $R_5$ is selected from among $C_1$-$C_6$ alkyl, and $C_6$-$C_{10}$ aryl; and n and m are selected independently from 0 to 4, with the proviso that m and n cannot be 0 at the same time.

The foregoing precursors can be usefully employed with a suitable titanium precursor to form titanate films of barium, strontium, tantalum and/or lanthanum, e.g. by ALD, CVD or other suitable deposition process.

In one embodiment, wherein the precursor is $Ba(Cp)_2$, the precursor is used in a form that is not coordinated with any Lewis bases or other complexation agents, that is, without complexation with adduct-forming groups such as tetrahydrofuran, dienes, trienes, glymes, diglymes, triglymes, tetraglymes, etc.

Additionally, or alternatively, the R groups on the cyclopentadienyl rings of such $Ba(Cp)_2$ precursor may in specific embodiments be constituted to exclude the following substituent combinations as being identically present on each of the two cyclopentadienyl rings: (i) wherein $R_1$-$R_5$ are all methyl, (ii) wherein three of such $R_1$-$R_5$ substituents are isopropyl and the remaining two of such substituents are H, (iii) wherein three of such $R_1$-$R_5$ substituents are t-butyl and the remaining two of such substituents are H, (iv) wherein four of such $R_1$-$R_5$ substituents are methyl and the remaining substituent is $(Me)_2NCH_2CH_2$—, and (v) wherein four of such $R_1$-$R_5$ substituents are methyl and the remaining substituent is $EtOCH_2CH_2$— where Et is ethyl.

Correspondingly, the $Sr(Cp)_2$ precursor may be selected in specific embodiments wherein at least one of the following criteria are met: (a) the precursor is not coordinated with tetrahydrofuran, and (b) $R_1$-$R_5$ are selected to exclude the following substituent combinations as being identically present on each of the two cyclopentadienyl rings: (i) wherein $R_1$-$R_5$ are all methyl, and (ii) wherein three of such $R_1$-$R_5$ substituents are isopropyl and the remaining two of such substituents are H.

In another embodiment, the invention contemplates $Sr(Cp)_2$ compounds that are uncoordinated with any complexation agents.

In yet another embodiment, the precursor compounds of the invention may be stabilized with Lewis base ligands, subject to the exceptions stated in the preceding paragraphs. Lewis bases suitable for such purpose include, without limitation, alkenes, dienes, cycloalkenes, cyclooctatetraenes, alkynes, substituted alkynes (symmetrical or asymmetrical), amines, diamines, triamines, tetraamines, polyamines, ethers, diglymes, triglymes, tetraglymes, tetramethyl sulfides, dialkylsulfides, ethylenediamine, vinyltrimethylsilane, allyltrimethylsilane, and pentamethyl diethylenetriamine.

In one embodiment, the cyclopentadienyl ligand includes a ligand formed according to the following reaction (wherein the second reactant and final ligand are represented with kappa (κ) donor notation):

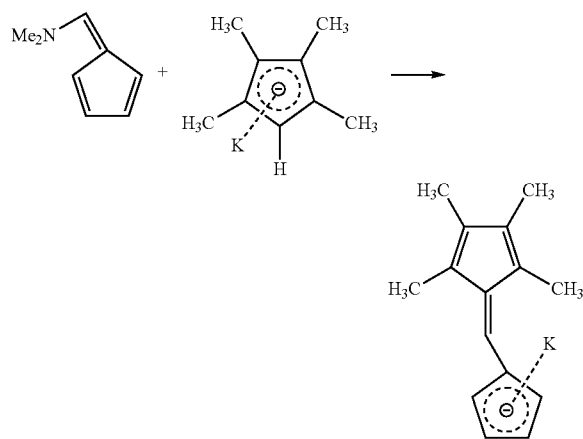

The precursors of the invention may be supplied in any suitable form for volatilization to produce the precursor vapor for deposition contacting with the substrate, e.g., in a liquid form that is vaporized or as a solid that is dissolved or suspended in a solvent medium for flash vaporization, as a sublimable solid, or as a solid having sufficient vapor pressure to render it suitable for vapor delivery to the deposition chamber, or in any other suitable form.

When solvents are employed for delivery of the precursors of the invention, any suitable solvent media can be employed in which the precursor can be dissolved or dispersed for delivery. By way of example, the solvent medium may be a single-component solvent or a multicomponent solvent mixture, including solvent species such as $C_3$-$C_{12}$ alkanes, $C_2$-$C_{12}$ ethers, $C_6$-$C_{12}$ aromatics, $C_7$-$C_{16}$ arylalkanes, $C_{10}$-$C_{25}$ arylcycloalkanes, and further alkyl-substituted forms of aromatic, arylalkane and arylcycloalkane species, wherein the further alkyl substituents in the case of multiple alkyl substituents may be the same as or different from one another and wherein each is independently selected from $C_1$-$C_8$ alkyl. Particularly preferred solvents include alkanes, alkyl-substituted benzene compounds, benzocyclohexane (tetralin), alkyl-substituted benzocyclohexane and ethers, with tetrahydrofuran, xylene, 1,4-tertbutyltoluene, 1,3-diisopropylbenzene, tetralin, dimethyltetralin, octane and decane being particularly preferred solvent species.

In instances where liquid delivery is employed in deposition processes of the invention to form deposited metal films, it may be preferable to utilize high boiling point solvents in order to avoid metal precursor deposits in the delivery system, such as in flow circuitry, and in vaporizers that are utilized to volatilize the metal precursor to form a corresponding precursor vapor, where the system is otherwise susceptible to solids deposition and clogging. For example, in delivery systems utilizing low boiling solvents for delivery of the precursor, e.g., a strontium precursor for liquid delivery atomic layer deposition, residual precursor of solution in the vaporizer and delivery lines will evaporate leaving behind solid precursor. Eventually such precursor builds up and clogs the delivery system.

Accordingly, in various embodiments of the invention, it may be desirable to utilize high boiling aromatic solvents, e.g., aromatic solvents having a boiling point at 1 atmosphere pressure in a range of from about 140° C. to about 250° C. For example, in liquid delivery strontium precursor applications for atomic layer deposition processes, suitable solvents may include xylene, 1,4-tertbutyltoluene, 1,3-diisopropylbenzene, tetralin, dimethyltetralin and other alkyl-substituted aromatic solvents.

In general, the precursor compositions of the invention may alternatively comprise, consist, or consist essentially of any of the components and functional moieties discloses herein, in specific embodiments of the invention.

The titanium precursors useful with the barium, strontium, tantalum and/or lanthanum precursors of the invention include those of the formula $X_2TiCp_2$, where Cp is the same as described above, and each X is independently selected from among chlorine, bromine, iodine, $C_1$-$C_4$ alkyl and $C_1$-$C_4$ alkoxy, dialkylamido (such as those of the formula $R_1R_2N$—, where $R_1$ and $R_2$ are independently selected from $C_1$-$C_4$ alkyls,) and cyclic alkylamido (such as those of the formula $(CH_2)_yN$—, where y is an integer selected from among 2, 3, 4, 5 and 6).

Because both $MCp_2$ and $X_2TiCp_2$ are highly sensitive to hydroxyl-terminated surfaces, such precursors react readily to form respective self-limiting monolayers on substrate surfaces such as semiconductor wafers having free hydroxyl functionality thereon. MO and $TiO_2$ can be deposited sequentially from these precursors, and post-annealed to achieve various dielectrics, e.g., strontium titanate (STO) dielectrics, lanthanum titanate (LTO) dielectrics, barium titanate (BTO) dielectrics and barium strontium titanate (BSTO) dielectrics.

The cyclopentadienyl precursors of the invention are particularly useful in atomic deposition layer processes, such as the illustrative process schematically represented in FIG. 1.

As shown in FIG. 1, a silicon substrate 10 is shown as having a noble metal electrode 12 thereon (Step 1). This structure then is subjected to contact with titanium precursor of the formula $TiR_2X_2$ under suitable deposition conditions to form a structure (Step 2) in which the noble metal electrode 10 is functionalized on its upper surface with titanium moieties. The thus-functionalized structure then is submitted to contact with an oxidant [O] such as oxygen, ozone, etc., or water. A wide variety of oxidants can be used for such purpose. The surface then reacts with the oxidant to form a hydroxylated surface (Step 3).

The hydroxylated surface of the device structure next is contacted with the strontium reagent, $Sr(Cp)_2$, to yield the strontiated (strontium-functionalized) surface (Step 4). The strontiated surface then is contacted with oxidant or water to form the hydroxylated surface (Step 5), and the hydroxylated surface thereafter is processed by contact with the titanium precursor, with repetition of the above-described steps (Steps 2-5) any suitable number of times to build up a layer 14 of strontium titanate, $SrTiO_3$ (Step 6).

In this repetitive manner, a dielectric film of strontium titanate is built up over the electrode layer in the device structure, with the deposition process being conducted through multiple steps of titanium functionalization, hydroxylation, strontiation and hydroxylation, to build up the strontium titanate film to a desired thickness.

Analogous processes can be carried out utilizing alternating layers of Ba, Sr, and Ti, Ba and Sr mixtures and Ti, La and Ta, and La and Ti.

In one embodiment of such process, the oxidant is selected from among oxygen, ozone and oxygen plasma. The use of such oxidant may eliminate the need for a final annealing step, such as rapid thermal annealing.

In general, the thickness of the titanate layer in the practice of the present invention can be of any suitable value. In a specific embodiment of the invention, the thickness of the titanate layer can be in a range of from 5 nm to 500 nm or more.

The titanium precursors usefully employed in the broad practice of the invention can be of any suitable type, and include, without limitation, the aforementioned $Cp_2TiX_2$, as well as titanium alkoxides, $Ti(OR)_4$, such as $Ti(OPr-i)_4$ and $Ti(OBu-t)_4$, and titanium beta-diketonate alkoxides, $Ti(\beta\text{-diketonate})_2(OR)_2$, such as $Ti(thd)_2(OPr-i)_2$ and $Ti(thd)_2(OBu-t)_2$.

Figure 2:
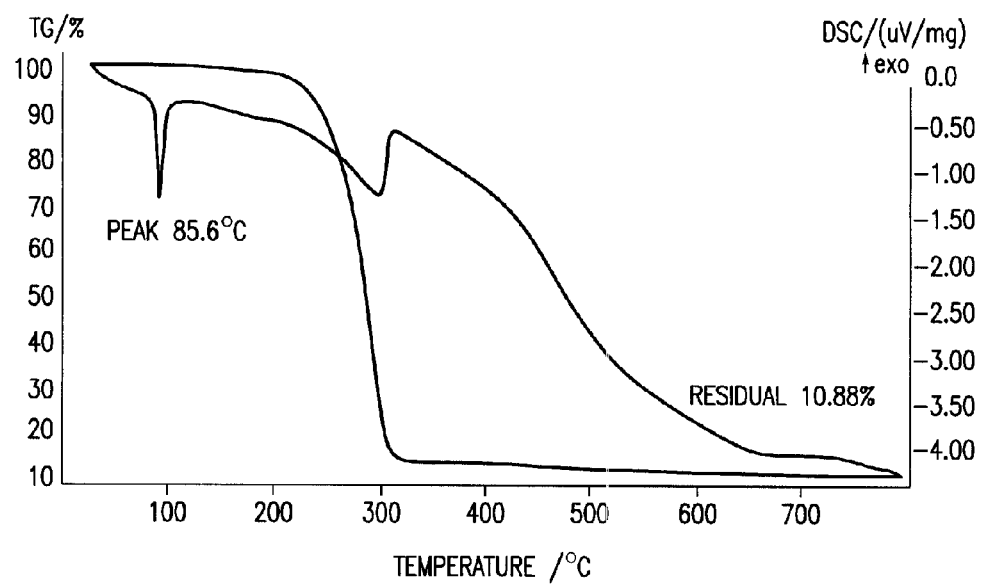
FIG. 2 is a graph of thermal analysis data including thermogravimetric (TG) analysis and differential scanning calorimetry (DSC) data as a function of temperature, for Ba[(N—Pr)Me$_4$Cp]$_2$ exhibiting a melting endotherm at 85.5° C. and a residue of 10.88%.

One preferred reagent for forming a titanate film is $Ba[(n-Pr)Me_4Cp]_2$. FIG. 2 is a graph of thermal analysis data including thermogravimetric (TG) analysis and differential scanning calorimetry (DSC) data, as a function of temperature, for $Ba[(n-Pr)Me_4Cp]_2$, exhibiting a melting endotherm at 85.5° C. and a residue of 10.88%.

Figure 3:
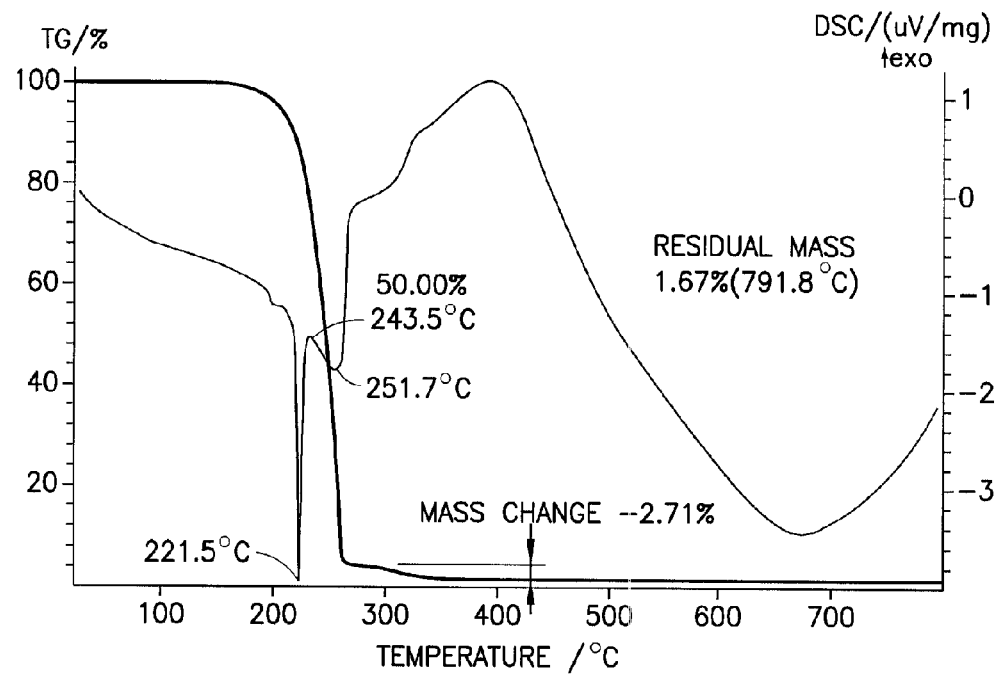
FIG. 3 is a graph of thermal analysis data of Sr(Cp*)$_2$ including TG and DSC data as a function of temperature, wherein Cp* is pentamethylcyclopentadienyl.

Another preferred strontium precursor in the practice of the present invention is bis(pentamethylcyclopentadienyl) strontium. FIG. 3 is a graph of thermal analysis data including TG and DSC data as a function of temperature, for $Sr(Cp^*)_2$, wherein $Cp^*$ is pentamethylcyclopentadienyl.

The strontium, lanthanum, tantalum and barium precursors of the invention may be provided in any suitable packaged form, as appropriate to storage of the precursor and its subsequent delivery in use. In one embodiment, the precursor package comprises a vessel defining a closed interior volume holding the precursor, with the vessel having a valve head assembly connected thereto. The valve head assembly may include a manual or automatic valve controller, to modulate the position of a valve element in the value head assembly, between a fully opened and a fully closed position, as required for storage and dispensing use of the package.

In general, the precursor may be provided in a form appropriate for delivery and use, e.g., in a form for liquid delivery or alternatively for solid precursor delivery of vapor.

Figure 4:
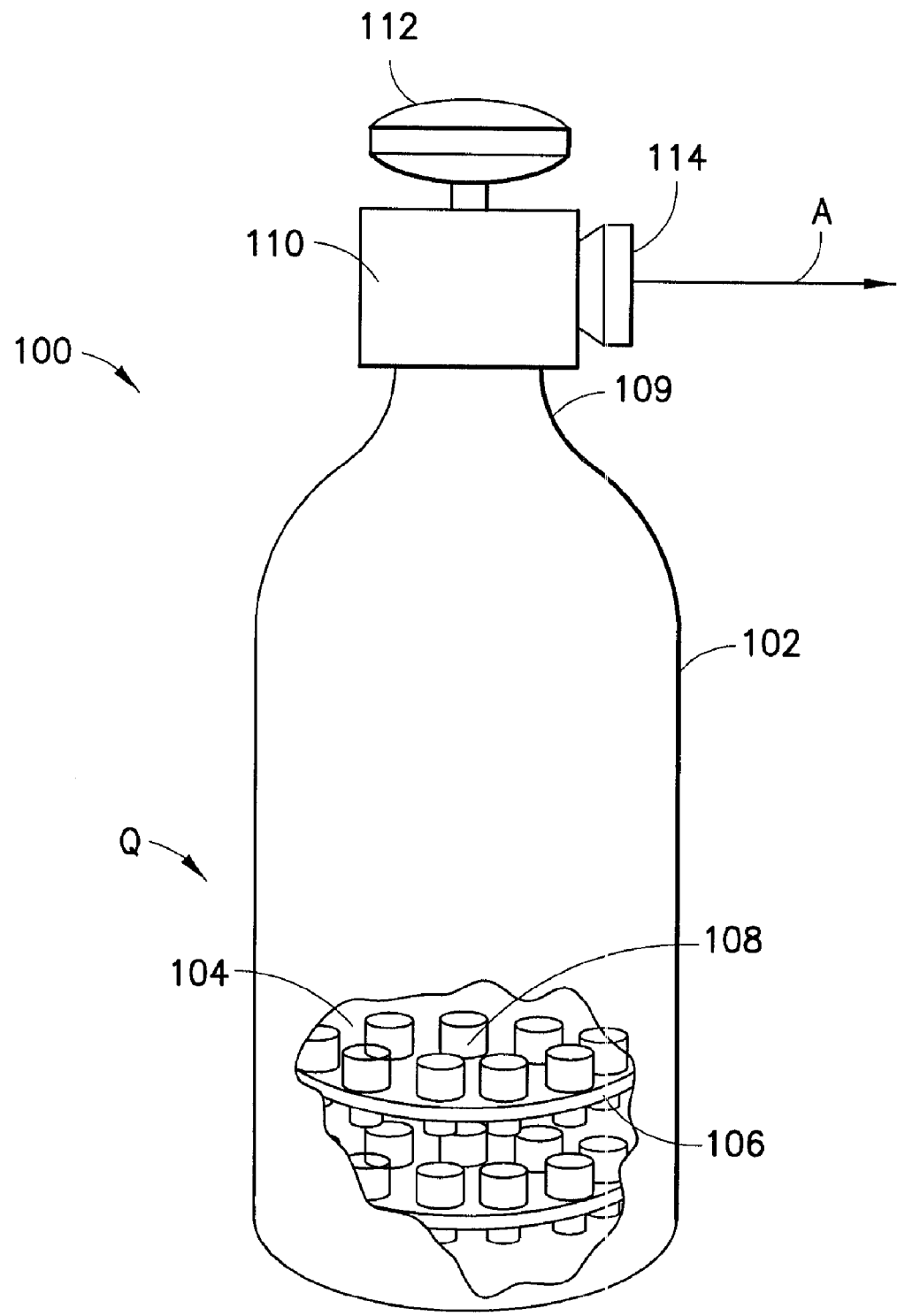
FIG. 4 is a schematic representation of a material storage and dispensing package containing a barium, strontium or lanthanum precursor according to the present invention, in one embodiment thereof.

FIG. 4 is a schematic representation of a material storage and dispensing package 100 containing a barium, strontium, tantalum or lanthanum precursor, according to one embodiment of the present invention.

The material storage and dispensing package 100 includes a vessel 102 that may for example be of generally cylindrical shape as illustrated, defining an interior volume 104 therein. In this specific embodiment, the barium or strontium precursor is a solid at ambient temperature conditions, and such precursor may be supported on surfaces of the trays 106 disposed in the interior volume 104 of the vessel, with the trays having flow passage conduits 108 associated therewith, for flow of vapor upwardly in the vessel to the valve head assembly, for dispensing in use of the vessel.

The solid precursor can be coated on interior surfaces in the interior volume of the vessel, e.g., on the surfaces of the trays 106 and conduits 108. Such coating may be effected by introduction of the precursor into the vessel in a vapor form from which the solid precursor is condensed in a film on the surfaces in the vessel. Alternatively, the precursor solid may be dissolved or suspended in a solvent medium and deposited on surfaces in the interior volume of the vessel by solvent evaporation. For such purpose, the vessel may contain substrate articles or elements that provide additional surface area in the vessel for support of the precursor film thereon.

As a still further alternative, the solid precursor may be provided in granular or finely divided form, which is poured into the vessel to be retained on the top supporting surfaces of the respective trays 106 therein.

The vessel 102 has a neck portion 109 to which is joined the valve head assembly 110. The valve head assembly is equipped with a hand wheel 112 in the embodiment shown. The valve head assembly 110 includes a dispensing port 114, which may be configured for coupling to a fitting or connection element to join flow circuitry to the vessel. Such flow circuitry is schematically represented by arrow A in FIG. 4, and the flow circuitry may be coupled to a downstream ALD or chemical vapor deposition chamber (not shown in FIG. 4).

In use, the vessel 102 is heated, such input of heat being schematically shown by the reference arrow Q, so that solid precursor in the vessel is at least partially volatilized to provide precursor vapor. The precursor vapor is discharged from the vessel through the valve passages in the valve head assembly 110 when the hand wheel 112 is translated to an open valve position, whereupon vapor deriving from the precursor is dispensed into the flow circuitry schematically indicated by arrow A.

In lieu of solid delivery of the precursor, the precursor may be provided in a solvent medium, forming a solution or suspension. Such precursor-containing solvent composition then may be delivered by liquid delivery and flash vaporized to produce a precursor vapor. The precursor vapor is contacted with a substrate under deposition conditions, to deposit the metal, e.g., strontium, barium, tantalum and/or lanthanum, on the substrate as a film thereon.

In one embodiment, the precursor is dissolved in an ionic liquid medium, from which precursor vapor is withdrawn from the ionic liquid solution under dispensing conditions.

As a still further alternative, the precursor may be stored in an adsorbed state on a suitable solid-phase physical adsorbent storage medium in the interior volume of the vessel. In use, the precursor vapor is dispensed from the vessel under dispensing conditions involving desorption of the adsorbed precursor from the solid-phase physical adsorbent storage medium.

Supply vessels for precursor delivery may be of widely varying type, and may employ vessels such as those commercially available from ATMI, Inc. (Danbury, Conn.) under the trademarks SDS, SAGE, VAC, VACSorb, and ProE-Vap, as may be appropriate in a given storage and dispensing application for a particular precursor of the invention.

The precursors of the invention thus may be employed to form precursor vapor for contacting with a substrate to deposit a thin film of barium, strontium, tantalum or lanthanum thereon, in connection with concurrent or sequential deposition of titanium from a suitable titanium source reagent, to produce titanate films as barium titanate, lanthanum titanate, tantalum titanate, strontium titanate, and barium strontium titanate.

In a preferred aspect, the invention utilizes the barium, strontium, tantalum and/or lanthanum precursors to conduct atomic layer deposition in connection with the use of a suitable titanium source reagent, yielding ALD films of superior high dielectric character that are uniformly coated on the substrate with high step coverage even on high aspect ratio structures.

Accordingly, the barium, strontium, tantalum and lanthanum precursors of the present invention enable a wide variety of microelectronic devices, e.g., semiconductor products, flat panel displays, etc., to be fabricated with high dielectric constant titanate films of superior quality.

The features and advantages of the invention are more fully shown by the following non-limiting example.

EXAMPLE 1

In the synthesis of bis(pentamethylcyclopentadienyl) strontium ((Cp*)$_2$Sr), potassium pentamethylcyclopentadiene (KCp*, 5.11 grams, 29.29 mmol) was added to a stirred suspension of strontium diiodide (SrI$_2$, 5.00 grams, 14.64 mmol) in 300 ml of diethyl ether. The mixture was stirred for 48 hours, filtered, and concentrated in vacuo giving 4.10 grams of the bis(pentamethylcyclopentadienyl)strontium diethyl ether adduct ((Cp*)$_2$Sr(OEt$_2$)). The coordinated diethyl ether was removed by a toluene reflux process. In a typical, but non-limiting example, 3.00 grams of (Cp*)$_2$Sr (OEt$_2$) were dissolved in 150 ml of toluene. The toluene solution was heated to 110° C. and the toluene/diethyl ether removed slowly in vacuo giving an off yellow solid. This process was repeated three more times to give the ether free (Cp*)$_2$Sr. High purity (Cp*)$_2$Sr can be obtained by sublimation at 120-130° C.

An atomic layer deposition process is carried out as generally schematically shown in FIG. 1, in which the process involves pulsing of a titanium source into the deposition reactor, purging the reactor to remove excess titanium precursor, then pulsing water vapor into the reactor, with or without oxidant (such as O$_2$, O$_3$ or N$_2$O,) followed by pulsing the strontium source into the reactor and then purging, followed by introduction of water vapor with or without oxidant. This process is repeated until a desired film thickness of the strontium titanate layer is reached. Deposition temperature is advantageously in a range of from 250° C. to 500° C. Pulse rates can be on the order from 10 milliseconds to 30 seconds or more. After deposition, the film may require rapid thermal annealing (RTA) to obtain a crystalline SrTiO$_3$ film, by RTA treatment at temperature in a range of from 500° C. to 900° C., for an annealing period of from a few seconds to 30 minutes or more. An oxygen plasma may be used in the reactant step, in addition to or in lieu of the forgoing annealing treatment.

Corresponding synthesis can be carried out to form other cyclopentadienyl compounds of the invention, e.g., tantalum compounds.

While the invention has been disclosed herein with respect to particular illustrative embodiments, aspects and features, it will be recognized that the invention is not thus limited, but rather extends to and encompasses other variations, modifications and alternative embodiments, as will readily suggest themselves to those of ordinary skill in the art based on the disclosure herein. Accordingly, the claims set out hereinafter are intended to be construed to encompass all such variations, modifications and alternative embodiments, as being within the spirit and scope of such claims.

What is claimed is:

1. A method of depositing a thin film on a substrate, said method comprising
    contacting the substrate with a vapor of a precursor composition, wherein the precursor composition includes a compound of the formula M(Cp)$_2$ wherein M(Cp)$_2$ is bis(tetramethyl-n-propylcyclopentadienyl) strontium, and wherein the compound is not coordinated with tetrahydrofuran, to form a thin film comprising strontium on the substrate; and
    contacting the thin film comprising strontium with an oxidant selected from the group consisting of oxygen, ozone and water.

2. The method according to claim 1, comprising chemical vapor deposition or atomic layer deposition.

3. The method according to claim 2, comprising chemical vapor deposition.

4. The method according to claim 2, comprising atomic layer deposition.

5. The method according to claim 1, further comprising concurrent or sequential deposition of titanium from a titanium source reagent to produce a titanate film.

6. The method according to claim 5, wherein the titanate film is strontium titanate.

7. The method according to claim 5, comprising concurrent deposition.

8. The method according to claim 5, comprising sequential deposition.

9. The method according to claim 1, further comprising a solvent medium.

10. The method according to claim 9, wherein the solvent medium comprises a solvent species selected from the group consisting of C$_3$-C$_{12}$ alkanes, C$_2$-C$_{12}$ ethers, C$_6$-C$_{12}$ aromatics, C$_7$-C$_{16}$ arylalkanes, C$_{10}$-C$_{25}$ arylcycloalkanes, and further alkyl-substituted forms of aromatic, arylalkane and arylcycloalkane species, wherein the further alkyl substituents in the case of multiple alkyl substituents may be the same as or different from one another and wherein each is independently selected from C$_1$-C$_8$ alkyl.

11. The method according to claim 9, wherein the solvent medium is tetrahydrofuran, xylene, 1,4-tertbutyltoluene, 1,3-diisopropylbenzene, tetrahydronaphthalene, dihydrodimethylnaphthalene, octane or decane.

12. The method according to claim 5, wherein the oxidant is oxygen or ozone.

13. The method according to claim 12, wherein the titanate film produced is not annealed.

* * * * *